US005770460A

United States Patent [19]
Pawlak et al.

[11] Patent Number: 5,770,460
[45] Date of Patent: Jun. 23, 1998

[54] ONE-STEP LATERAL FLOW NONBIBULOUS ASSAY

[75] Inventors: Catherine Pawlak, Cardiff; Allan D. Pronovost; Keren Goins, both of San Diego, all of Calif.

[73] Assignee: Quidel Corporation, San Diego, Calif.

[21] Appl. No.: 486,807

[22] Filed: Jun. 7, 1995

Related U.S. Application Data

[63] Continuation of Ser. No. 156,877, Nov. 23, 1993, which is a continuation of Ser. No. 639,967, Jan. 11, 1991.

[51] Int. Cl.$^6$ .................. G01N 33/76; G01N 33/543; G01N 33/531; G01N 33/566
[52] U.S. Cl. .................. 436/510; 435/7.25; 435/7.5; 436/514; 436/520; 436/525; 436/532; 436/533; 436/534; 436/535; 436/548; 436/807; 436/810; 436/814; 436/829; 422/56; 422/61
[58] Field of Search .................. 422/56, 61; 436/510, 436/514, 520, 525, 532, 533, 534, 535, 807, 810, 829, 548, 814; 435/7.25, 7.5

[56] References Cited

U.S. PATENT DOCUMENTS

| | | | |
|---|---|---|---|
| 3,933,589 | 1/1976 | Keyes | 435/176 |
| 4,094,647 | 6/1978 | Deutsch et al. | 422/56 |
| 4,168,146 | 9/1979 | Grubb et al. | 435/7.92 |
| 4,235,601 | 11/1980 | Deutsch et al. | 422/56 |
| 4,323,536 | 4/1982 | Columbus et al. | 422/56 |
| 4,351,824 | 9/1982 | Lehrer | 424/12 |
| 4,361,537 | 11/1982 | Deutsch et al. | 422/56 |
| 4,435,504 | 3/1984 | Zuk et al. | 435/7 |
| 4,572,901 | 2/1986 | Ceriani et al. | 436/528 |
| 4,623,461 | 11/1986 | Hossom et al. | 210/445 |
| 4,693,834 | 9/1987 | Hossom | 210/767 |
| 4,703,017 | 10/1987 | Campbell et al. | 436/501 |
| 4,707,453 | 11/1987 | Wagner et al. | 436/501 |
| 4,729,961 | 3/1988 | Avrameas et al. | 436/501 |
| 4,740,475 | 4/1988 | Paul | 436/165 |
| 4,775,636 | 10/1988 | Moeremans et al. | 436/518 |
| 4,826,760 | 5/1989 | Privitera | 435/7 |
| 4,855,240 | 8/1989 | Rosenstein et al. | 436/514 |
| 4,857,453 | 8/1989 | Ullman et al. | 435/7 |
| 4,861,711 | 8/1989 | Friesen et al. | 436/7.5 |
| 4,943,522 | 7/1990 | Eisinger et al. | 435/7 |
| 5,120,643 | 6/1992 | Ching et al. | 435/7.92 |
| 5,135,872 | 8/1992 | Pouletty et al. | 436/180 |
| 5,141,850 | 8/1992 | Cole et al. | 436/525 |
| 5,169,757 | 12/1992 | Yamazaki et al. | 435/7.92 |
| 5,559,041 | 9/1996 | Kang et al. | 436/518 |

FOREIGN PATENT DOCUMENTS

| | | | |
|---|---|---|---|
| 0158746 | 10/1985 | European Pat. Off. | G01N 33/553 |
| 0191640 | 8/1986 | European Pat. Off. | G01N 33/52 |
| 2 209 378 | 1/1987 | European Pat. Off. | |
| 0276152 | 7/1988 | European Pat. Off. | G01N 33/558 |
| 0 284 232 | 9/1988 | European Pat. Off. | |
| 0 296 724 | 12/1988 | European Pat. Off. | |
| 0 306 772 | 3/1989 | European Pat. Off. | |
| 2204398 | 11/1988 | United Kingdom | G01N 33/532 |

OTHER PUBLICATIONS

Catalog Product Brochure for hCG Urine Test, Pacific, Biotech, Inc., San Diego, CA, 3 pp. total.
Catalog Product Brochrue for Clearview Strep A Test, Sequoia–Turner Corporation, Mountain View, CA, 2 pp. total.
Catalog Product Brochure for Clearview hCG Test, Sequoia–Turner Corporation, Mountain View, CA, 2 pp. total.
Catalog Product Brochure for hCG Urine Plus Test, Abbot Laboratories, Abbott, IL, 3 pp. total.
Catalog Product Brochure for Clearview Chlamydia Test Kit, Clearview and Unipath, 3 pp. total.
Catalog Product Brochure for (EPT) Early Pregnancy Test Kit, Parke–Davis, Morris Palms, NJ, 2 pp. total.

*Primary Examiner*—Michael P. Woodward
*Attorney, Agent, or Firm*—Morrison & Foerster

[57] ABSTRACT

A particularly efficient design for a nonbibulous lateral flow one step assay for an analyte in a biological sample is disclosed. In the improved device of the invention, three zones which are in nonbibulous lateral flow contact are employed: a sample receiving zone, a labeling zone, and a capture zone. The sample containing analyte is carried through the labeling zone and interacts with an assay label comprising visible moieties, preferably particles, which are coupled to specific binding reagent for analyte or to a competitor with analyte for a capture reagent. The flow continues into the capture zone where the visible moieties to which analyte or competitor are coupled are captured. Excess fluid is absorbed into an absorbent zone in contact with the capture zone. A positive result is obtained by visualizing the visible moieties in the capture zone. An additional improvement comprises obtaining the nonbibulous lateral flow by converting a bibulous support to a nonbibulous support through coating with a blocking agent, such a methylated BSA. Control label comprising visible moieties (preferably, visually distinguishable from those of the assay label) may also be included in the labeling zone and captured in a separate control portion of the capture zone to verify that the flow of liquid is as expected.

11 Claims, 2 Drawing Sheets

ONE-STEP LATERAL FLOW NONBIBULOUS ASSAY

This application is a continuation of application Ser. No. 08/156,877 filed 23 Nov. 1993, which is a file wrapper continuation of Ser. No. 07/639,967 filed 11 Jan. 1991.

TECHNICAL FIELD

The invention relates to immunological and related assay methods and apparatus, especially to those for testing biological samples using sandwich or competitive assays.

BACKGROUND ART

The literature on various forms of specific binding assays, especially immunoassays, is extensive and commercial products are numerous. A large number of simplified and conveniently packaged assays are currently marketed, and patent protection has been sought for a large number of these.

Of particular interest in connection with the invention herein are those assays which are conducted using a lateral flow protocol. U.S. Pat. No. 4,943,522 issued 24 Jul. 1990, incorporated herein by reference, sets forth citations which describe such devices and methods. This patent itself is directed to a lateral flow device which relies on a nonbibulous support to conduct liquids from one portion of the device to another. The present invention represents an improvement on this method and device wherein nonbibulous lateral flow is used to conduct visible moieties, especially labeled particles, e.g., dyed latex, red blood cells or liposomes capable of reacting with analyte or a competitor thereto into a capture zone for detection, using a bibulous support made nonbibulous by treatment with a blocking agent. The result is a one-step assay which can be conducted in a very short period of time (typically, within 60 seconds), and wherein the readout is usually available instantaneously upon the sample contacting a capture zone.

Other disclosures of lateral flow assays have also appeared. For example, U.S. Pat. No. 4,861,711, issued 29 Aug. 1989 describes a lateral flow assay wherein all components needed for the detection of an analyte are embedded in a single sheet. The lateral flow is referred to as chromatographic behavior. European patent application 306,772 published 15 Mar. 1989 describes a lateral flow device which comprises a chromatographic medium wherein the zone for application of sample and the reaction zone with an immobilized reagent capable of binding the analyte or a label-specific binding material are separated. British application 2,204,398 published 9 Nov. 1988 and assigned to Unilever describes a lateral flow device wherein sample applied to the device picks up labeled reagent and permeates into a detection zone. Labels include gold sols and colored particles. U.S. Pat. No. 4,168,146 describes lateral flow through a test strip; the presence of an analyte is determined by addition of a suitable color indicator.

European application 276,152 published 27 Jul. 1988 and assigned to Symbiotics Corp. describes a bibulous matrix lateral flow device which operates on two separate planes. U.S. Pat. Nos. 4,094,647; 4,235,601 and 4,361,537, all assigned to Thyroid Diagnostics Inc. describe chromatographic strips which, when placed in developing fluid, move a sample through a series of zones for binding to reagent and detection. U.S. Pat. No. 4,857,453 assigned to Syntex describes a device wherein reagents are supplied in breakable containers which are integral to the device.

EP 158,746 and U.S. Pat. No. 4,775,636 assigned to Janssen describe the use of metal sols as visible detecting labels for specific binding assays.

U.S. Pat. No. 4,703,017, assigned to Becton Dickinson, describes test strip devices wherein binders for an analyte and/or a visible tracer are applied to defined areas of a solid support by adsorption or covalent coupling. After application of the binder to one or more test areas of the substrate, the residual binding capacity of the test substrate is saturated or blocked by treatment with one or more types of proteins which do not specifically bind the materials to be employed in the assay. The tracer, when bound under assay conditions to the binder or to the analyte bound to the binder, is visible on the support without further treatment. The test strip is contacted and incubated with a sample containing (or suspected of containing) analyte; a sample strip may be provided with a plurality of test areas. U.S. Pat. No. 4,855,240, also assigned to Becton Dickinson, describes an assay wherein a sample and a tracer as described in U.S. Pat. No. 4,703,017 are applied at disparate locations on a flat lateral flow device.

With the exception of the first mentioned U.S. Pat. No. 4,943,522, all of the lateral flow methods heretofore discussed employ bibulous supports. The bibulous nature of the support increases the time of the assay and permits obtaining a result only after 5 minutes or more. The advantages of immediate availability of results conferred by the methods and devices of the present invention result from the conversion of the bibulous to a nonbibulous support in all regions of the matrix and from the design and miniaturization of the device as a whole.

DISCLOSURE OF THE INVENTION

The invention provides rapid and accurate methods for assessing the presence or absence of analytes in biological samples and devices for the conduct of these methods.

Thus, in one aspect, the invention is directed to an assay device for determination of the presence or absence of an analyte in a biological sample wherein the device comprises a sample receiving zone comprising a solid support capable of conducting non-bibulous lateral flow of sample in contact with a labeling zone capable of conducting nonbibulous lateral flow and containing visible moieties coupled to either a specific binding partner reactive with the analyte or a ligand competitive with analyte for binding to a capture reagent, which labeling zone is in turn in nonbibulous lateral flow contact with a capture zone, also capable of conducting nonbibulous lateral flow and containing a specific binding partner for the visible moiety to which analyte has been attached or which is attached to competitor. The zones can be on the same solid support or on contiguous separate supports or matrices. The three zones are in nonbibulous lateral flow contact in the sense that they permit lateral nonbibulous liquid flow between them. The sample application, labeling and capture zones also permit liquid to flow through the zones themselves by nonbibulous lateral flow. The capture zone is contiguous with a means for absorbing liquid and particles that have flowed through all three zones. The sample receiving zone may further serve to remove debris or interfering substances from the sample by physical entrapment without impeding the nonbibulous lateral flow.

In another aspect, the invention is directed to a method to conduct one-step assays which comprises applying a sample containing or suspected of containing an analyte to the sample receiving zone of the invention apparatus. In still another aspect, the invention is directed to methods to prepare the apparatus of the invention, and to improved nonbibulous matrices obtained by treating bibulous matrices with blocking agents.

BRIEF DESCRIPTION OF THE DRAWINGS (A more detailed description of the drawings follows in the Examples section.)

MODES OF CARRYING OUT THE INVENTION

Figure 1:
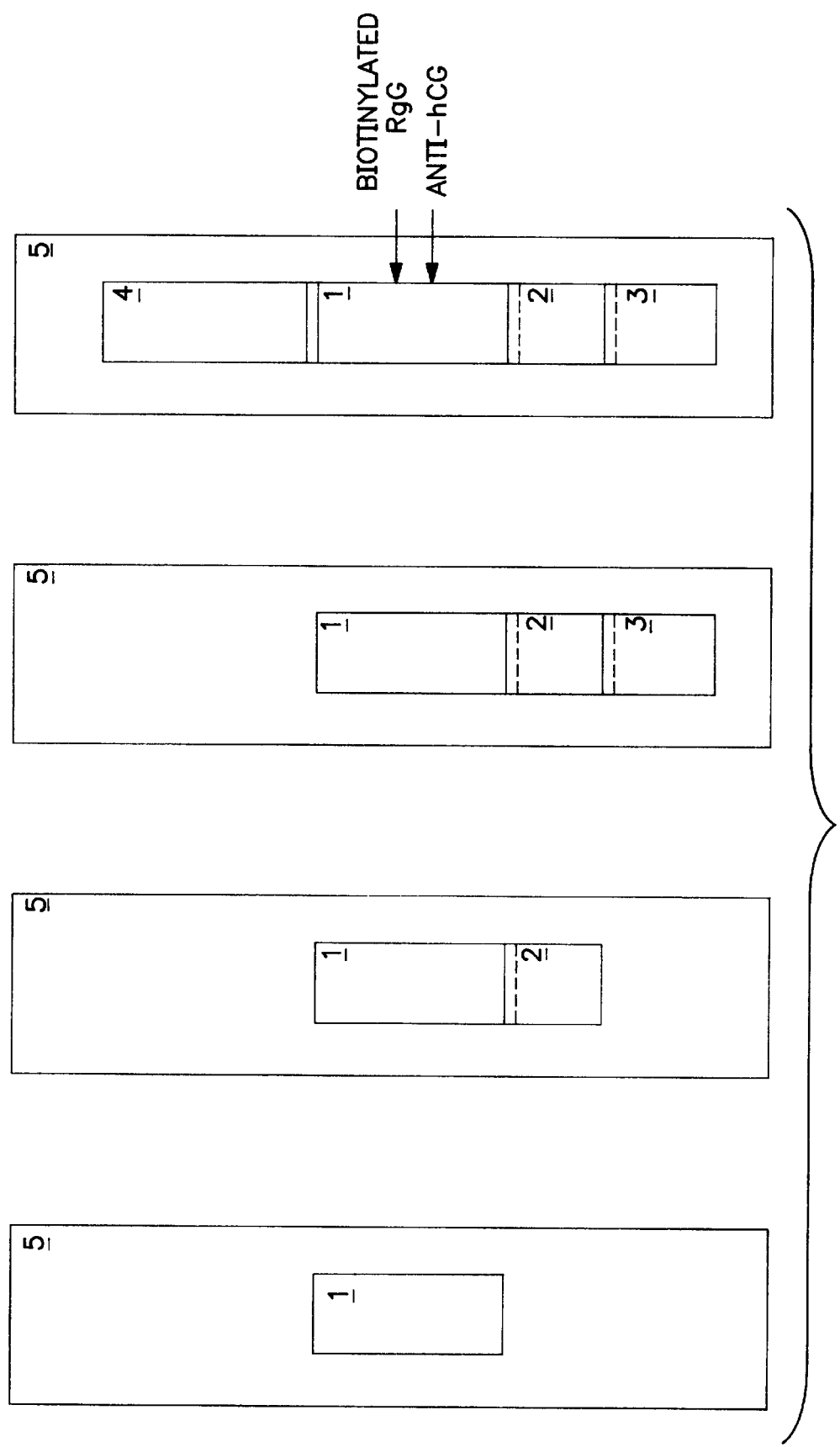
FIG. 1 shows steps in the assembly of one embodiment of the lateral flow portion of the apparatus of the invention.

The invention concerns improvements in assays which are conducted on supports which conduct nonbibulous lateral flow of fluids. As defined in the above-referenced U.S. Pat. No. 4,943,522, "nonbibulous" lateral flow refers to liquid flow in which all of the dissolved or dispersed components of the liquid which are not permanently entrapped or "filtered out" are carried at substantially equal rates and with relatively unimpaired flow laterally through the membrane or support. This is distinguished from preferential retention of one or more components as would occur, for example, in materials capable of absorbing or "imbibing" one or more components, as occurs in chromatographic separations. "Bibulous" materials include untreated forms of paper, nitrocellulose and the like which effect chromatographic separation of components contained in liquids which are passed therethrough.

Bibulous materials, however, can be converted to those which exhibit nonbibulous flow characteristics by the application of blocking agents, in particular certain detergents and proteins, which obscure the interactive forces that account for the bibulous nature of the supports per se. Thus, nonbibulous materials include those which are intrinsically capable of conducting nonbibulous flow, such as porous polyethylene sheets or other inert materials or can be comprised of bibulous materials which have been blocked. Preferred blocking agents include bovine serum albumin, either per se or in methylated or succinylated form, whole animal sera, such as horse serum or fetal calf serum, and other blood proteins. Other protein blocking agents include casein and non-fat dry milk.

Detergent-based blocking agents can also be used. The types of detergents which are appropriate are selected from nonionic, cationic, anionic and amphoteric forms, and the selection is based on the nature of the membrane being blocked. Considerations which govern the selection of the appropriate detergent blocking agent are well understood in the art. It is preferred to use detergents in combination with protein-based blocking agents. Suitable detergents which can be used either alone or in admixture with the protein blocking agents include polyoxyethylene sorbitan alcohol detergents (i.e., the Tween series), polyoxyethylene alcohols such as Nonidet P-40 or polyoxyethylene ethers such as Triton X-100. The selection of blocking agent and formulation of the blocking composition is important, as the blocking must be sufficient to effect nonbibulous flow, but the modified surface must not interfere with analyte-label-capture interaction.

One improvement which is the basis for the present invention is the use of, in the assay devices herein or in assay devices which utilize nonbibulous lateral flow in general, matrices or supports that are formed by the conversion of membranes or other supports with bibulous characteristics to nonbibulous membranes or supports. This is effected through application of blocking solutions. While intrinsically nonbibulous supports, such as the polyethylene sheet material manufactured by Porex Technologies Corporation (described in the above-referenced U.S. Pat. No. 4,943,522), can be employed in lateral flow assays, the use of converted microporous bibulous supports is preferred and has some advantages, such as more efficient immobilization of a capture binding reagent and resulting increased sensitivity, improved lateral flow, and enhanced speed of detection.

To convert a bibulous support such as paper or nitrocellulose to a support capable of effecting nonbibulous lateral flow, the original support is treated with a solution of the blocking agent in an effective concentration to dispose of unwanted reactivities at the surface. In general, this treatment is conducted with a blocking solution, such as a protein solution of 1–20 mg/ml protein at approximately room temperature for several minutes—several hours. The resulting coated material is then permanently adsorbed to the surface by air-drying, lyophilization, or other drying methods.

A further improvement in the assay devices of the invention lies in the design of the essay itself. The invention assay devices comprise four distinct zones, at least three of which conduct nonbibulous lateral flow. The device is designed so that the sample containing analyte is applied to a sample receiving zone and then flowed through a labeling zone into a capture zone. The capture zone is in turn in contact with a means for removing excess liquid sample. In general, this will consist of an absorbent, such as filter paper or glass fiber filter, which is generally bibulous in nature.

Selection of the carrier porous material and its treatment is done with consideration of the specific function each zone performs in the assay device.

The sample-receiving zone serves simply to begin the flow of analyte-containing sample and for this reason should be constructed of a material of low analyte retention. One means to impart this property is to impregnate the sample receiving zone with a neutral protein-blocking reagent, followed by treatment to immobilize the blocking agent (e.g., lyophilization). An additional advantage of this treatment is increased wetability and wicking action, speeding the transfer of the sample into the labeling zone. The sample-receiving zone may also function as a mechanical filter, entrapping any undesirable particulates present in the sample.

The labeling zone contains visible moieties which can be detected if accumulated in the capture zone. The visible moieties can be simply dyes or dye polymers which are visible when present in sufficient quantity, or can be, and are preferred to be, particles such as dyed latex beads, liposomes, or metallic, organic, inorganic or dye sols, dyed or colored cells or organisms, red blood cells and the like. Means for including various dyes within liposomes are well known, and have been disclosed, for example, in U.S. Pat. No. 4,695,554 as utilized in the examples below.

The visible moieties used in the assay provide the means for detection of the nature of and quantity of result, and accordingly, their appearance in the capture zone must be a function of the analyte in the sample. In general, this can be provided for by coupling the visible moieties to a ligand which binds specifically to analyte, or which competes with analyte for a capture reagent in the capture zone. In the first approach, the visible moieties are coupled to a specific binding partner which binds the analyte specifically. For example, if the analyte is an antigen, an antibody specific for this antigen may be used; immunologically reactive fragments of the antibody, such as $F(ab')_2$, Fab or Fab' can also be used. These visible moieties, or "test" visible moieties, then bind to analyte in the sample as the sample passes through the labeling zone and are carried into the capture zone by the liquid flow. When the complexes reach the capture zone, a capture reagent, which is then specific for analyte, such as an antibody or fragment thereof as set forth above, retains those coupled conjugates to which analyte has been bound, and permits those which do not contain analyte to pass into the absorbent zone. In the second approach, the visible moieties are coupled to a ligand which is competitive with analyte for a capture reagent in the capture zone, most typically, other molecules of the analyte itself. Both the analyte from the sample and the competitor bound to the visible moieties are then carried into the capture zone. Both analyte and its competitor then react with the capture reagent, which in this instance is also typically specifically reactive with analyte (and its competitor). The unlabeled analyte thus is able to reduce the quantity of competitor-conjugated visible moieties which are retained in the capture zone. This reduction in retention of the visible moieties becomes a measure of the analyte in the sample.

The labeling zone may also include "control" visible moieties which do not contain the specific binding agent or analyte competitor and which are also carried through to a control area of the capture zone by the liquid flow. These control visible moieties are coupled to a control reagent which binds to a capture partner specific for it and can then be captured in a separate "control" portion of the capture zone to verify that the flow of liquid is as expected. The visible moieties used in the control may be the same or different color than those used for the test moieties. If different colors are used, ease of reading the results is enhanced.

In all of the above, employment of the selected blocking agent together with colored moieties in the labeling zone followed by the immobilization of the blocking agent on the support (by, e.g., a freeze-drying process) is of utmost importance for improved performance of the device. It is well known that visible moieties, especially particles, aggregate upon air-drying and do not readily rehydrate in contact with a liquid sample. Therefore, absent conversion to the nonbibulous surface, instead of being transported to the capture zone with the sample, the visible moieties will remain trapped in the labeling zone.

As the analyte labeled with the visible moieties or the labeled competitor pass through the capture zone, the labeled analyte or competitor are bound to at least a portion of the membrane in the capture zone (the "test" portion) through the interaction of a specific reagent applied therein which reacts directly with the analyte or competitor bound to the test visible moieties. If control visible moieties are used, provision is made for their capture in the capture zone in an area separate from that where the test visible moieties will be bound. The control visible moieties, preferably of a different color from their "test" counterparts, are provided with a control binding agent which is specific not for analyte or the test capture reagent, but for a material in a capture area in the capture zone which represents a control band. Thus they are directly detected in a separate "control" portion. For example, in the procedures exemplified below, the labeling control beads include streptavidin and their control band portion in the capture zone contains biotin, which couples to avidin specifically. Other "irrelevant" binding pairs can also be used—such as antigen/antibody reactions unrelated to analyte.

The experimental results are read in the capture zone by noting the presence or absence of a visible signal at the location of the capture zone for the test visible moieties. The use of a control region is helpful in that appearance of a color in the control region signals the time at which the test result can be read, even for a negative result. Thus, when the expected color appears in the control region, the presence or absence of a color in the test region can be noted. The use of different colors for test and control regions aids in this process.

The use of the matrix which is bibulous inherently, but convertible to a nonbibulous flow characteristic is particularly useful in the creation of this capture zone. Capture reagents can be applied to the matrix before the application of blocking agent and immobilized in situ, obviating the need for an activation treatment as frequently required for attachment of capture reagents to bibulous supports. At this stage, the bibulous nature of the matrix during the coupling of the capture reagents may be advantageous. However, the blocking/washing treatment which converts the bibulous membrane to nonbibulous support provides unimpaired and speedy flow of all components of the system.

The speed of the assay, which requires less than one minute and provides in many instances essentially an instantaneous result as the sample flows through the capture zone, is attainable because of the nonbibulous nature of the zones and of the short distance the sample must traverse in each zone. Miniaturization of the diagnostic device results in the remarkable speed of the assay, well below the times disclosed in similar lateral flow assays, such as those described in U.S. Pat. No. 4,361,637; U.S. Pat. No. 4,861,711; U.S. Pat. No. 4,740,468; and European patent 0 306 772 A. Miniaturization permits instantaneous results which are observable as soon as the sample contacts the capture zone and which occur almost immediately or within 60 seconds of the addition of the sample to the sample receiving zone. The speed of appearance and intensity of the positive visible reaction seen depends on the concentration of analyte in the sample. The speed of appearance of the positive visual reaction can be adjusted to provide the optimal visual result with concentrations of analyte of clinical importance and adjusted to suit the timing needs of the end-user.

Suitable analytes to which the method of the invention can be applied are any for which a specific binding partner can be found. In general, most analytes of medical and biological significance can find specific binding partners in antibodies prepared against them or fragments of these antibodies. Suitable analytes include soluble analytes such as hormones, enzymes, lipoproteins, bacterial or viral antigens, immunoglobulins, lymphokines, cytokines, drugs, soluble cancer antigens, and the like. These analytes include various proteins such as protamines, histones, porphorylated proteins, nucleoproteins, and so forth such as, for example, transcortin, erythropoietin, transferrin, various globulins, thyroxin-binding globulin, the immunoglobulins of various subclasses A, G, D, E, and M, various complement factors, blood clotting factors such as fibrinogen, Factor VIII, tissue thromboplastin, and thrombin.

Also included are hormones such as insulin, glucagon, relaxin, thyrotropin, somatotropin, gonadotropin, follicle-stimulating hormone, gastrin, bradykinin, vasopressin, and various releasing factors. A wide range or antigenic polysaccharides can also be determined such as those from *Chlamydia, Neisseria aonorrheae, Pasteurella Destis, Shigella dysentereae*, and certain fungi such as Mycosporum and Aspergillus. Another major group comprises oligonucleotide sequences which react specifically with other oligonucleotides or protein targets. An extensive list of soluble analytes determinable in the method of the invention is found in U.S. Pat. No. 3,996,345, which is incorporated herein by reference.

The following examples are intended to illustrate but not to limit the invention.

EXAMPLE 1
Preparation of a Bead Labeled One-step Assay Device for Human Chorionic Gonadotropin (hCG)

The test device has three active components—a sample receiving zone, a labeling zone containing a particulate label and a capture zone. The three active portions, which communicate through nonbibulous liquid flow, are assembled so as to take advantage of a means to absorb or remove excess liquid which has been transported through these three zones, and to support the active components of the device. The construction is as follows.

Preparation of the Sample Receiving Zone

The sample receiving zone is prepared from Sontara 0-100 DuPont Orlon spunlace fabric. The fabric is rendered nonbibulous by saturating with methylated bovine serum albumin (methylated BSA). The conversion to nonbibulous material is achieved by treatment at 47.6 $\mu$l/cm$^2$ with a 10 mg/ml solution of the methylated BSA at room temperature at five minutes. The pad of Sontara is then frozen at $-70°$ C. along with a lyophilization flask for at least an hour. The Sontara membrane is then lyophilized overnight on a Virtis Freezemobile. The treated sample receiving zone is then nonbibulous, and is cut into 10×7.5 mm rectangles with the spunlace fibers being parallel to the longer side of the pad.

Preparation of the Labeling Zone

To prepare the labeled control beads for inclusion in the labeling zone, 0.5 ml of blue latex beads initially suspended at a weight/vol concentration of 2.5% are washed twice with glycine-buffered saline (GBS) (100 mM glycine, 171 mM NaCl). The beads are sonicated for 10 minutes in contact with the GBS and then microcentrifuged for three minutes.

The pelleted beads are treated with 0.5 ml coupling solution which consists of 0.4 mg/ml streptavidin and 0.2 mg/ml methylated BSA in GBS. The pelleted beads are resuspended and sonicated for 10 minutes, and then rotated overnight at room temperature.

The bead preparation is then centrifuged for three minutes and the supernatant removed by aspiration. The bead pellet is then resuspended in 0.5 ml of the 10 mg/ml methylated BSA. This mixture is rotated end over end for four hours at room temperature, and the bead preparation centrifuged to recover the pellet. The supernatant is aspirated and the pellet is washed three times with bead storage solution which consists of 1 mg/ml methylated BSA in 50 mM Tris, pH 8. The final bead preparation is prepared in a bead storage solution at a concentration of 1% solids. The resulting beads will be conducted by nonbibulous flow through the capture zone described below. They have been reacted so as to bind to a biotin-containing capture band. "Test" beads for labeling analyte, containing monoclonal anti-hCG, are prepared in similar manner as follows:

One-half (0.5) ml of red latex beads (it is preferred that the control and test beads are of different colors) are washed twice with 1 ml GBS as described above by sonicating for 10 minutes and recovered by microcentrifugation for three minutes. To the pelleted beads is added 0.5 ml of coupling solution, in this case consisting of 0.8 mg/ml monoclonal anti-hCG and 0.2 mg/ml methylated BSA in GBS. The pellet is resuspended and sonicated for 10 minutes, and then rotated overnight at room temperature. After centrifugation for three minutes, the supernatant is aspirated and the bead pellet is resuspended in 0.5 ml of the 10 mg/ml methylated BSA and rotated end over end for four hours at room temperature. After centrifugation and removal of the supernatant, the pellet is washed three times with bead storage solution as described above, and the final bead preparation is at a concentration of 1% solids.

Finally, to prepare the labeling zone containing both test and control beads the test beads are diluted into methylated BSA at a concentration of 0.06% solids and the control beads into the same solution at 0.02% solids. The resultant mixture is stirred and poured onto a Sontara O-100 DuPont spunlace fabric membrane at 47.6 $\mu$l/cm$^2$. The labeled pad is then kept at room temperature for five minutes and frozen at $-70°$ C., along with the lyophilizing flask for at least an hour. The resulting membranes are lyophilized overnight on Virtis Freezemobile. The label-containing pads are then cut into 10×7.5 mm rectangles with the spunlace fibers parallel to the longer side of the pad.

Preparation of Capture Zone Membrane

To prepare the capture zone membrane, nitrocellulose is rendered nonbibulous as follows. Nitrocellulose obtained from Schleicher and Schuell, having a pore size of 8–12 $\mu$m, is affixed to a chart recorder and hCG capture bands are dispensed as 2-cm-spaced parallel lines using a solution of 2 mg/ml rabbit anti-hCG (purified by protein A) in Tris buffer using the Tri-Dac dispense system operated in the manual mode with valve pressure at 70 psi, container pressure setting at 5 psi, fluid flow at 15 sec/drop, chart speed at 500 mm/minute. These are lines reactive with the test beads. The membrane is then spotted in parallel lines 0.3 cm above the previously-spotted anti-hCG capture zone with a 0.6 mg/ml biotinylated rabbit gamma globulin solution dissolved in Tris buffer. These are lines reactive with the streptavidin on the control beads. After air drying for 10–30 minutes, the membrane is placed onto a tray containing blocking buffer (10 mg/ml methylated BSA in 50 mM Tris) for 15 minutes at room temperature. The membrane is removed and blotted and then transferred to a tray containing wash buffer (50 mM Tris maleate, pH 5.4) for 5 minutes at room temperature. The blocked and washed membrane is then blotted, allowed to air dry, stored in a desiccator at room temperature until assembly of the device.

Assembly of the Device

A 20×7.5 mm strip of the capture zone membrane, shown as component 1 in FIG. 1, is affixed centrally on an adhesive transparency strip shown as component 5 in FIG. 1. The transparency strip is a 700×17 mm strip of P 2200 3M transparency made adhesive with double-sided adhesive tape 444 (3M).

The pad containing visible label, shown as component 2 in FIG. 1, is then affixed next to the capture zone pad with a 1 mm overlap as shown in FIG. 1. The sample receiving pad, shown as component 3, is then placed next to label-containing pad with 1 mm overlap, as shown in the figure.

The device is then provided with an absorbent pad, which is a 20×7.5 mm rectangle of ED No. 939 absorbent, which is affixed to the distal end of the capture zone membrane with a 1 mm overlap, as shown in the figure.

Figure 2:
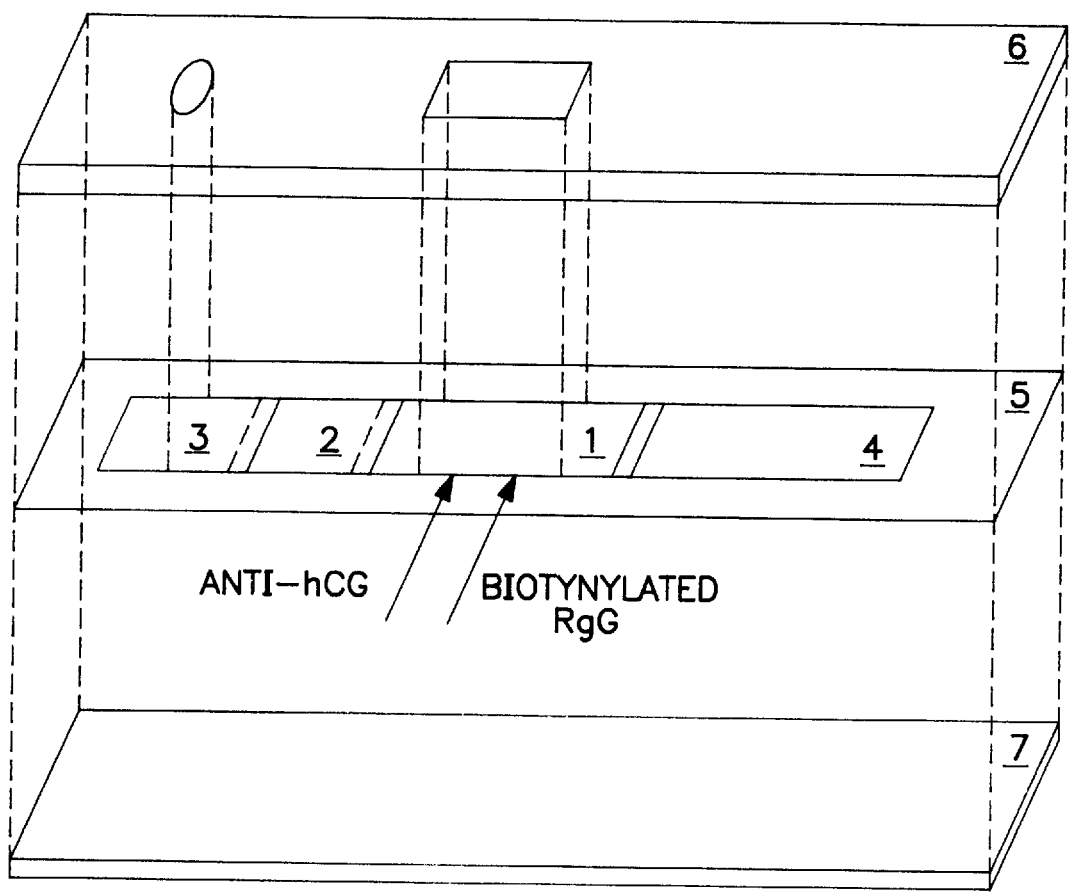
FIG. 2 shows the assembly of an invention device placing the lateral flow plate in a casing.

The resulting test strip on the transparency backing is then covered with a plastic top, shown as component 6 in FIG. 2, with the length of the strip being centrally within the groove of the plastic top. Both sets of capture lines are exposed in the viewing window, and the sample application hole is immediately above the sample receiving pad. Finally, the bottom of the device, which is a 700×17 mm bottom strip of 1 mm thick opaque white plastic made adhesive with double-sided adhesive tape (3M) is attached to the other side of the transparency strip.

EXAMPLE 2
Preparation of a Liposome-Based Device

In a manner analogous to that set forth in Example 1, the counterpart liposome-containing device is prepared. The preparation of the sample receiving pad, the capture zone membrane, and the assembly of the components on backing is identical to that set forth in Example 1. The labeled liposome-containing zone pad is prepared as follows:

Liposomes are prepared according to the procedures set forth in U.S. Pat. No. 695,554 and contain sulforhodamine dye. Different colored dyes are used for control and test liposomes.

For test liposomes, monoclonal anti-hCG, which has been purified from ascites, is used. Ascites is 50% SAS cut at 4° C. and desalted on a G-25 column into 10 mM Tris. The antibodies are then further purified on a Q-Sepharose Fast Flow column using a salt gradient of 0–0.5M sodium chloride in 10 mM Tris. The fractions are monitored at 280 nm, and the peaks collected and buffered exchanged into 1M sodium phosphate.

The antibody is diluted to 3 mg/ml and 8.5 molar equivalents of SPDP is added. The solution is incubated for 30 minutes at 27° C. and buffer exchanged on G25 and 0.1M sodium acetate. The material is reduced with 1M DTT in sodium acetate to give a final concentration of 50 mM and incubated at 27° for 25 minutes and then buffer exchanged on G25 with Tris acetate buffer. The relative amounts of liposomes and antibody are determined assuming 8 µmol of phosphorus per mg of antibody and 1 µmol of phosphorus is supplied for 1 ml of uncoupled liposomes. The liposomes are then titrated to pH 8 with 1M Tris and coupled with antibody for two hours at 27° C.

The resulting antibody-conjugated liposomes are sized on a C6 Fast Flow column diluted in liposome storage buffer to an absorbance of 0.25 units at 565 nm.

The liposome-containing pad is then prepared by saturating a Sontara pad with a liquid solution of anti-hCG conjugated liposomes diluted to an absorbance at 565 nm of 0.06 at 35 µl to a 10×7.5 mm assay pad. The liposome storage buffer for this dilution contains 10% sucrose and 10 mg/ml methylated BSA. The labeling pads are kept at room temperature for 5 minutes and frozen at −70° C. along with the lyophilizing flask for at least an hour. The membranes are then lyophilized overnight in a Virtis Freezemobile.

EXAMPLE 3

Conduct of an hCG Assay

The device of Example 1 is placed flat on a benchtop and two drops of sample at approximately 30 µl per drop are applied to the sample receiving zone. The liquid is allowed to flow through the three zones in nonbibulous lateral flow contact to the absorbent zone, with a blue control band appearing in the upper portion of the viewing window in less than a minute. If hCG is present in the sample at least 50 mIU/ml, an additional red band in the hCG capture region is visible.

We claim:

1. An assay device for detection of the presence or absence of an analyte in a liquid sample,
   wherein all dissolved or dispersed components of said assay flow through the device at substantially equal rates
   wherein the assay comprises the binding of at least a portion of the analyte to a specific binding partner for said analyte,
   wherein said assay device comprises four separately prepared elements in lateral flow contact, said elements consisting essentially of:
   (a) a sample receiving zone comprising a lyophilized solid support matrix which conducts nonbibulous lateral flow of the liquid sample, said sample receiving zone being in nonbibulous lateral flow contact with
   (b) a labeling zone comprising a solid support matrix which conducts lateral nonbibulous flow of the liquid sample which has been prepared by treating a bibulous support matrix with at least one assay label comprising visible moieties coupled to a ligand which specifically binds to analyte to form a visible complex or competes with the analyte for binding to a capture reagent in the presence of an amount of methylated bovine serum albumin effective as a blocking agent which modifies the flow characteristics of said bibulous support matrix so as to render it nonbibulous, followed by lyophilizing said treated matrix, said labeling zone being in nonbibulous lateral flow contact with
   (c) a capture zone comprising a solid support matrix which conducts nonbibulous lateral flow which contains in at least a portion thereof at least one capture reagent capable of binding said visible complex or said competing ligand bound to visible moieties wherein said capture zone has been prepared by adsorbing said capture reagent in said portion on a bibulous support matrix followed by treating said matrix with an amount of methylated bovine serum albumin effective as a blocking agent which modifies the flow characteristics of said bibulous support matrix so as to render it nonbibulous, followed by air drying, said capture zone being contiguous with and in flow contact with
   (d) an absorbent zone,
   whereby said visible complex or said competing ligand bound to visible moieties is captured in said portion of the capture zone.

2. The device of claim 1 wherein the labeling zone further includes control label comprising visible moieties coupled to a control binding reagent, and wherein said capture zone further includes a specific binding partner for said control binding reagent in a portion of said capture zone different from that wherein said capture reagent for the analyte is located.

3. The device of claim 2 wherein said control reagent is avidin or a derivative thereof and wherein said specific binding partner for the control reagent is biotin.

4. The device of claim 2 wherein said assay label and control label are visually distinguishable.

5. The device of claim 4 wherein said assay label and control label are of different colors.

6. The device of claim 1 wherein said visible moieties are particles.

7. The device of claim 6 wherein said particles are colored latex beads, red blood cells, metal sols or liposomes containing dye.

8. A method to determine the presence or absence of analyte in a sample, which method comprises applying said sample to the sample receiving zone of the device of claim 1, so as to permit said sample to flow through the labeling zone and the capture zone into the absorbent zone, and
   detecting the presence or absence of visible moieties in the capture zone in said portion thereof containing the capture reagent capable of binding the analyte.

9. The method of claim 8 wherein said analyte is human chorionic gonadotropin (hCG).

10. The method of claim 9 wherein the specific binding partner for analyte is a monoclonal antibody immunoreactive with hCG.

11. A method to modify a bibulous lateral flow matrix for the conduct of specific binding assays on a liquid sample, wherein, in said bibulous matrix, one or more components of said assay dissolved or dispersed in a liquid sample is preferentially retained; which method comprises treating said bibulous matrix with an amount of methylated bovine serum albumin effective as a blocking agent to modify its flow characteristics so that all dissolved or dispersed components in said liquid sample flow at substantially equal rates through said modified matrix.

* * * * *